United States Patent [19]

Donohue

[11] 4,312,337
[45] Jan. 26, 1982

[54] CANNULA AND DRILL GUIDE APPARATUS

[76] Inventor: Brian T. Donohue, 21 Oak Dr., Oak Ridge, N.J. 07438

[21] Appl. No.: 185,277

[22] Filed: Sep. 8, 1980

[51] Int. Cl.³ .................. A61B 17/18; A61F 5/04; A61F 17/32; A61B 17/06
[52] U.S. Cl. .................. 128/92 EB; 128/92 E; 128/305.1; 128/310; 128/340
[58] Field of Search .......... 128/92 E, 92 EA, 92 EB, 128/92 B, 305.1, 310, 340

[56] References Cited

U.S. PATENT DOCUMENTS

| | | | |
|---|---|---|---|
| 349,791 | 8/1886 | Gibboney, Jr. | 128/340 |
| 1,641,077 | 8/1927 | Fouquet | 128/92 E |
| 3,090,386 | 5/1963 | Curtis | 128/340 |
| 3,349,772 | 10/1967 | Rygg | 128/340 |
| 3,946,740 | 3/1976 | Bassett | 128/340 |
| 4,265,231 | 5/1981 | Scheller, Jr. et al. | 128/305.1 |

FOREIGN PATENT DOCUMENTS 2344267  11/1977  France ................ 128/92 EB

OTHER PUBLICATIONS

Journal of Bone & Joint Surgery, "An Instrument to Aid in the Reduction of Bennett Fractures", O. C. Hudson, Oct. 1936, vol. 18, p. 1085.

*Primary Examiner*—Robert W. Michell
*Assistant Examiner*—C. W. Shedd

[57] ABSTRACT

A cannula and guide apparatus for use in drilling and wiring fractured bones having generally scissor-like handle arms pivotally joined and having jaw extensions beyond the pivot point. A hollow tubular cannula section is mounted on each jaw extension such that when the handle arms are closed, the cannula sections meet in interlocking engagement to provide one continual cannula. The cannula sections are generally arcuate shaped to fit within converging angular holes drilled through the cortex of the bone on each side of the fracture. When the cannula sections are engaged within the medula of the bone, a wire is fed through the cannula. After withdrawal of the stylet section the wire remains to be tied to complete the fracture wiring procedure. The cannula and guide apparatus may also be used for drilling holes for the wiring operation. A flexible cable having a drilling burr on one end thereof is inserted through the medial end of one cannula section and secured by a drill clamp to a drill motor. The complementary medial end of the other cannula section is capped with a tapered pin adapted to be received into a recess in the leading edge of the burr upon completion of drilling through a solid bone.

3 Claims, 4 Drawing Figures

CANNULA AND DRILL GUIDE APPARATUS

BACKGROUND OF THE INVENTION

1. Field of the Invention

This invention pertains to the field of surgical appliances and specifically to appliances used in the reduction of bone fractures. It includes a cannula through which a drilling burr secured to one end of a flexible shaft may be guided to drill holes in bones and then used to guide a wire to reduce the fracture, such that the disruption of surrounding muscle tissue and amount of wire used is minimal and a guide apparatus which positions the cannula precisely for minimal damage to surrounding tissues. It also pertains in general to the field of binding and cutting pliers.

2. Description of the Prior Art

This invention is designed to solve a specific problem which occurs in the reduction of fractures when the bone is wired together on both sides of the fracture. Fractured bones are frequently wired together to prevent rotational movement of the pieces during the healing process and to prevent distraction or separation of the fractured parts. In order to wire a fracture, an incision must be made in the area of the fracture, the soft tissue pulled away from the bone on both sides of the fracture and holes must be drilled through the cortex of the bone on each side of the fracture. Wire is then inserted through one hole, pulled through the medula and then out the other hole where it is tied. The problem with this procedure is that too much soft tissue is pulled away from the bone and damaged, and the blood supply to the bone is impaired. The instrument of the present invention is specifically designed to minimize the amount of soft tissue which needs to be separated from the bone and thereby insure an adequate supply of blood to the fractured parts. Further advantages include less trauma to the fracture site, less chance of post-operative infection and more rapid healing.

A search of the prior art reveals many patents in the field of wire binding and cutting pliers of a scissor or plier type such as those disclosed in U.S. Pat. Nos. 914,182; 1,304,620 and 1,641,077. There are also many prior patents on bone clamps, some of which use pins or wires and some of which are drill guides. Examples are U.S. Pat. Nos. 2,291,413; 2,834,342; 2,181,746; 2,583,896 and 2,455,609. None of these devices performs the same function as that of the present invention. Each has some problems associated with it which may not be obvious to the layman. For example, U.S. Pat. No. 2,455,609 teaches a wire applying forceps which initiates and adjusts a line loop to a desired completion. The device of this patent, which is commercially available, wraps a wire around (not through) a bone and a tight wire around a bone can cut off blood circulation to the bone. Other known devices have similar drawbacks.

The inventor knows of no surgical instrument which performs the functions of the device of this invention.

SUMMARY OF THE INVENTION

This invention pertains to a surgical cannula and guide apparatus for use in the reduction of bone fractures. As a wire guiding apparatus, the cannula includes two generally arcuate tubular sections of cannula secured at nearly a right angle to the ends of a scissors-like device in the same plane as its handle arms. These arcuate sections form a circular arc having a center located approximately at the pin of said arms. These sections are movable in opposition to each other in response to elongated scissor arms which are pivotally mounted to each other, one of said arcuate cannula sections engaging one another approximately on the longitudinal centerline of the device, such that when the arms are closed, said arcuate continuous cannula sections form one continual cannula of generally hemispherical shape. The scissor arms include detente means for locking the arms together and a spring means extended between said arms.

The procedure for use of the cannula and guide apparatus of the present invention is as follows. The bone is measured on each side of the fracture to determine optimum points for incision, drilling of holes and insertion of the cannula. Small incisions are made on each side of the fracture to permit the drilling of small angular holes through the cortex of the bone on each side of the fracture. With the scissors-like guide in its open position and the cannula sections separated, the interior ends of the arcuate cannula sections are inserted through the angular holes and the scissor-arms are gradually closed until the ends of the cannula engage. The arms are then locked in this position. A wire is then fed through the cannula and cut at each exterior end thereof. The cannula sections are then withdrawn from the bone by opening the scissor arms, the wire remaining looped in the bone. The wire ends are then tied and the excess cut. This procedure minimizes the amount of soft tissue which has to be separated from the bone because only that tissue around the two drilled holes need be disturbed. The procedure, therefore, maintains adequate blood circulation to the fractured parts and results in less trauma to the fracture site. It also results in less over-all post-operative infection and more rapid healing.

The cannula and guide apparatus of the present invention may also be used as a guide for drilling holes in bones at the angle and location required for proper reduction of the fracture with minimal damage to the surrounding tissue. This is particularly useful for the reduction of fractures in solid bones, such as a kneecap. To use the cannula guide apparatus as a drilling guide, a rotatable flexible cable having a small drill burr on one end thereof is inserted through the medial end of one of the cannula sections such that the drill burr abuts that medial end. A drill adaptable clamp is secured to the other end of the flexible cable and the clamp is then inserted into a drill motor. The medial end of the other cannula section is capped with a tapered pin adapted to be received into a recess in the leading edge of the drill burr. The cannula and guide apparatus of the present invention is thus configured to drill two holes sequentially in a bone having a soft medula or one hole in two sequential segments in a solid bone. The first hole or hole segment is drilled with the two handle sections in the open position. The burr guided by the cannula section in which its cable is inserted drills a hole along a path to the shape and length of the cannula. The cannula section and burr are then withdrawn and at this point one hole is drilled in a soft bone or one-half the hole is drilled in a solid bone. The cannula and guide apparatus is then rotated 180° and a hole or hole segment is similarly drilled on the other side of the fracture. In the second drilling operation, the section of the cannula having the tapered pin is inserted in the first drilled hole. As the drilling of the second hole is completed, the tapered pin on one cannula section engaged the recess on the leading edge of the burr to insure proper alignment of the holes or hole segments. After completion of the drilling procedure, the cannula sections are withdrawn, the drill burr, flexible cable and tapered pin are removed. The cannula and guide apparatus may now be used for feeding wire through the cannula sections for wiring the fracture as described above.

The precise size and shape of the cannula sections will depend on the size and shape of the bone on which it will be used. In some cases, it may be necessary to use different sizes of cannula for drilling and for wiring.

DESCRIPTION OF THE PREFERRED EMBODIMENT

Figure 1:
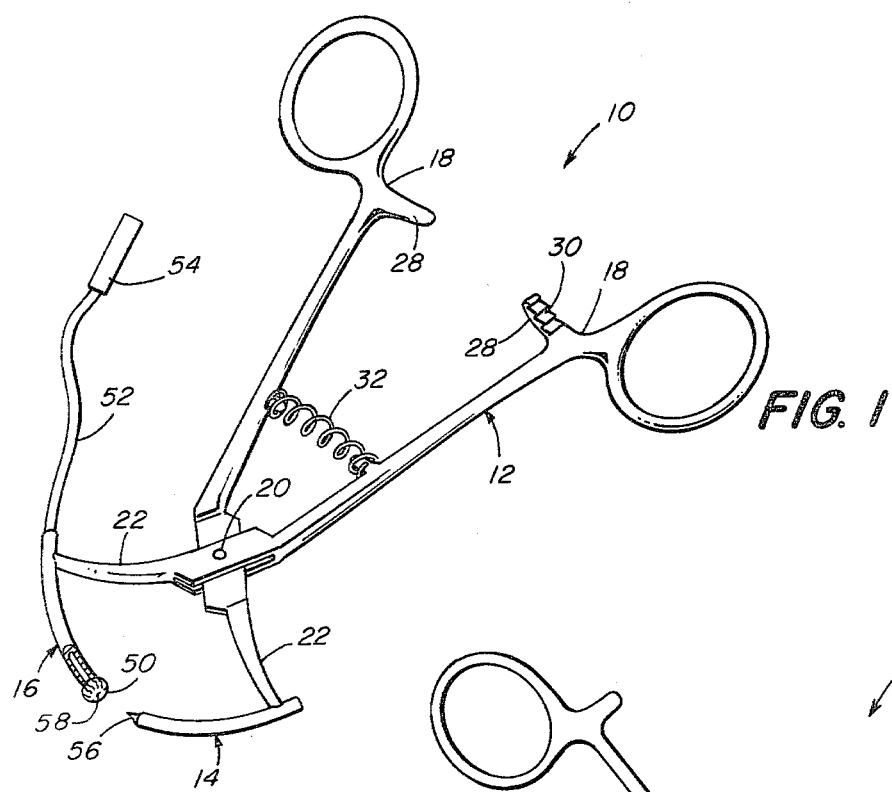
FIG. 1 is a top perspective view of the cannula and guide apparatus of the present invention configured for a drilling operation.

FIG. 1 is a top perspective view of the cannula and guide apparatus of the present invention, designated generally by the reference number 10. Apparatus 10 includes a guide portion 12 in the form of a scissors-like pivotal apparatus having two cooperating elongated handle sections 18 pivotally joined together at pivot 20 and having two cooperating jaw extensions 22 which serve as mounting and guiding means for two cannula sections 14, 16.

Figure 3:
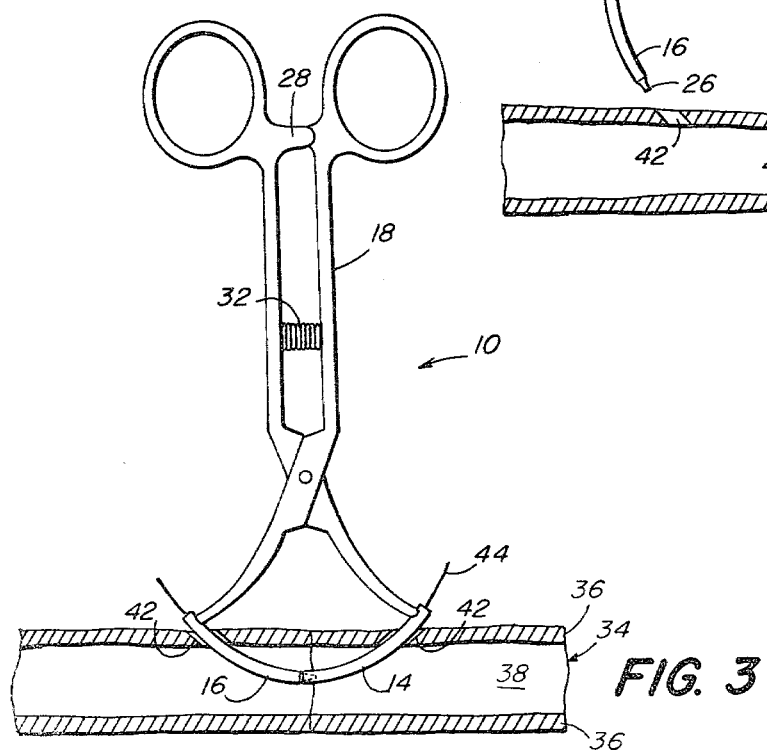
FIG. 3 is a top plan view of the cannula and guide apparatus of FIG. 1 in the fully closed position with both sections of the cannula engaged within the medula of a bone and a wire positioned through the cannula.
Figure 4:
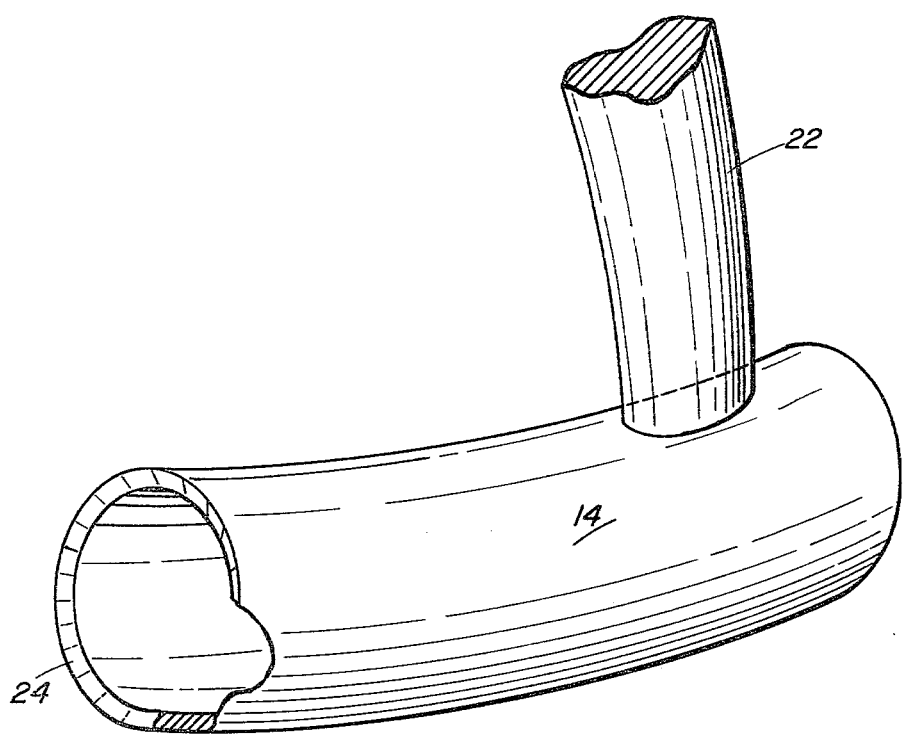
FIG. 4 is a perspective view of a portion of the cannula partially in section showing the chamfer interlock on the interior surface of the medial end.

Cannula sections 14, 16 are each two hollow, arcuate tubes open at both ends for the feeding of fine wire therethrough. Sections 14, 16 are secured at nearly a right angle to the ends of handle sections 18 in the same plane as said handle sections. Sections 14, 16 form a circular arc having a center located approximately at pivot pin 20 of said arms 18. These sections 14, 16 are movable in opposition to each other, their medial ends engaging on another. The medial end 24 of cannula section 14 is designed to snugly receive the medial end 26 of stylet section 16 when cannula and guide apparatus 10 is in its closed position (FIG. 3). Medial end 26 is a hollow portion having a chamfer on its interior surface so as to interlock with which the medial end 24 of cannula section 14 to insure one continued cannula when cannula and guide apparatus is in the closed position illustrated in FIG. 3. The shape precise shape of cannula sections 14, 16 will have to vary according to a number of factors. For the reduction of fractures in straight or relatively straight bones, stylet sections 14, 16 will generally be arcuate, the radius of the arc depending upon the diameter of the bone involved. For the reduction of some fractures, it is possible that cannula sections 14, 16 could be straight or angular, depending again on bone structure and shape.

Handle arms 18 are provided with means for locking said handle arms 18 in various closed or partially closed positions. Said locking means comprise an inward projecting member on each handle arm 18 slightly offset in the horizontal plane such that when the arms 18 are closed one of said members is positioned over the other. The two locking members have a series of cooperating detentes 30 in the form of angular ridges on their opposing sides such that when one locking member overlaps the other, these opposing detentes 30 will engage each other and lock handle arms 18 in a desired position. Slight pressure is required to change the locking position over the range of locking members 28.

A spring 32 may also be mounted between handle arms 18.

Cannula and guide apparatus 10 may also be used for drilling holes in bones. The embodiment of cannula and guide apparatus 10 illustrated in FIG. 1 shows apparatus 10 configured for a drilling operation. The cannula sections 14, 16 serve as guides for drilling holes 42 in the fractured bone 34 at the location and with the contour required for proper reduction of the the fracture with minimal damage to the surrounding tissue. This is particularly useful for the reduction of fractures in solid bones, such as a kneecap. To use cannula and guide apparatus 10 as a drilling guide, a rotatable flexible cable 52 having a small drilling burr 50 secured on one end thereof is inserted through the medial end 26 of cannula section 16 such that drill burr 50 abuts end 26. A drill adaptable clamp 54 is secured to the other end of flexible cable 52 and clamp 54 is inserted into a drill chuck (not shown). The medial end 24 of cannula section 14 is capped with a tapered pin 56 adapted to be received into a recess 58 in the leading edge of burr 50. Cannula and guide apparatus 10 is thus configured to drill two holes 42 sequentially in a bone 34 having a soft medula 38, or one continuous hole in two sequential complementary segments in a solid bone (not shown). The first hole 42 or hole segment is drilled with the two handle sections 18 in the open position. Burr 50 guided by cannula section 16 drills a hole 42 along a path to the shape and length of cannula section 16. After the desired hole 42 or hole segment is drilled, cannula section 16 and burr 50 are withdrawn from the drilled hole. At this point, one hole 42 is drilled in a soft bone 34, or one-half the hole is drilled in a solid bone. Stylet and guide apparatus 10 is then rotated 180° and the second hole 42 or hole segment is drilled similarly on the other side of the fracture. In the second drilling operation cannula section 14 having tapered pin 56 is inserted into the first drilled hole 42. As the drilling of the second hole segment in a solid bone is completed, tapered pin 56 engages recess 58 on the leading edge of burr 50 prevent the burr 50 from removing portions of the medial end of arcuate tube 14 during the drilling process. After completion of the drilling operation, cannula sections 14, 16 are withdrawn; drill burr 50, flexible cable 52 and tapered pin 56 are removed from cannula and guide apparatus 10. Cannula and guide apparatus 10 may now be used for wiring the fracture as described above.

It should be clearly understood that the precise size, shape, interior and exterior diameters of the cannula sections 14, 16 will depend on many factors such as the size, shape and thickness of the bone, the diameter of the wire required, the diameter of the flexible cable and the hardness of the bone. In some cases it may be necessary to use one size of cannula sections 14, 16 for drilling and another size for wiring.

Figure 2:
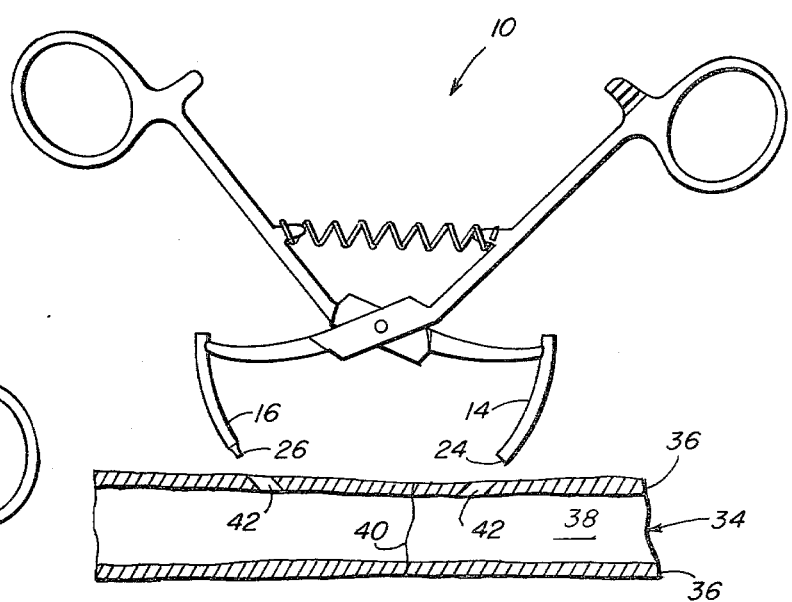
FIG. 2 is a top plan view of the cannula and guide apparatus of FIG. 1 in an open position showing the cannula sections just before penetration into angular holes in the cortex of a fractured bone.

FIGS. 2 and 3 illustrate the use of cannula and guide apparatus 10 in the wiring of bone fractures. A bone 34 is there shown having a hard cortex 36 and a soft medula 38 and a fracture indicated by the irregular line 40. Cannula and guide apparatus 10 is used to reduce the fracture by serving as a guide for wiring the parts of bone 36 together. To use apparatus 10, the bone 36 is carefully measured and two small incisions are made on either side of the fracture 40; the soft tissue removed from around two small areas of the bone. Angular or otherwise contoured holes 42 are then drilled through the cortex 36 of bone 34 such that the angles converge toward the fracture and such that cooperating cannula sections 14, 16 can be received through said holes 42 and meet in an engaged position in the medula 38 as shown in FIG. 3. In FIG. 2, cannula sections 14, 16 are shown in the position they would have just prior to entry or just subsequent to withdrawal from holes 42. Spring 32 is extended, thus biasing handle arms 18.

In the embodiment illustrated in FIGS. 2 and 3, the bone 36 is shown as a relatively straight bone and the cannula sections 14, 16 are arcuate in shape. The precise size and contours of cannula sections 14, 16 and holes 42 would depend on the shape and thickness of bone 36.

Also, in the embodiment shown in FIGS. 2 and 3, cannula section 16 is shown as having a chamfer on medial end 26 which serves as an interlocking means to insure one continual cannula when apparatus 10 is in the closed, wiring position illustrated in FIG. 3.

FIG. 3 illustrated cannula and guide apparatus 10 in its closed, operative position. Handle arms 18 are substantially parallel and locked in position by locking members 28. Spring 32 is exerting no tension. Cannula sections 14, 16 have fully penetrated holes 42 and are engaged within medula 38 to form one continuous cannula of generally arcuate shape. When stylet and guide apparatus 10 is in this position, a wire 44 may be fed through one open end of cannula section 14, through both cannula sections 14, 16 and out the other open end of stylet section 16. After the wire 44 has been placed therethrough, stylet and guide apparatus is opened as it is withdrawn, leaving a portion of wire 44 within the bone 34. At this point the cannula and guide apparatus will be in roughly the position shown in FIG. 2. The wire is then cut and tied as in normal practice. The procedure is then completed in a normal manner.

Cannula and guide apparatus 10 permits the wiring of fractured bone parts with a minimum of disruption to the soft tissue surrounding the bone and a minimum loss of blood circulation to the bone. Its use results in less trauma to the fracture site, less post-operative infection and more rapid healing.

As mentioned previously the size and shape of cannula sections 14, 16 will have to vary according to bone size, shape, and other factors. For those cannula sections 14, 16 which are generally arcuate in shape, the length of both sections varies from one-half circle to one-forth circle. Straight cannula sections would be used for some cases. The type of fracture could also have a bearing on the stylet section size and shape.

While I have described and illustrated herein one preferred embodiment of my invention, many other embodiments and modifications will occur to those skilled in the art. My invention includes all those embodiments falling within the scope and spirit of the appended claims.

I claim:

1. A surgical cannula and guide instrument for drilling holes and guiding wires therethrough, comprising;
    a guide portion having two elongated, scissor-like handle arms;
    said handle arms being pivotally secured to one another by a pivot pin;
    each of said handle arms having a jaw extension beyond the pivot junction;
    a hollow tubular cannula section secured to the outer end of each of said jaw extensions;
    one of said cannula sections having a chamfer on the interior surface of the medial end so as to form an interlock with the medial end of the other cannula section;
    said cannula sections having a size and shape and being mounted such that when said handle arms are pivoted to a closed position, said cannula sections become engaged and form one continual cannula;
    said cannula sections having a hollow interior such that a wire may be fed through said continual cannula.

2. The cannula and guide instrument of claim 1 wherein said cannula sections are generally arcuate in shape, secured to the jaw extensions of each of said handle arms at nearly a right angle and in the same plane as said handle arms, said arcuate sections forming a circular arc having a center located approximately at said pivot pin.

3. The cannula and guide instrument of claim 1 further including:
    a drilling burr;
    a rotatable flexible cable attached at one end to said drilling burr;
    said flexible cable capable of being fed through one of said cannula sections such that said burr abuts the medial end thereof;
    clamp means to secure the other end of said flexible cable to a drill motor;
    a tapered pin secured to the complementary medial end of the other cannula section;
    a recess in the leading edge of said burr to receive said tapered pin at the completion of a drilling operation to prevent said burr from removing portions of the medial end of said complementary cannula section.

* * * * *